(12) United States Patent
Shiono et al.

(10) Patent No.: US 9,086,343 B2
(45) Date of Patent: Jul. 21, 2015

(54) METHODS FOR OBSERVING SAMPLES AND PREPROCESSING THEREOF

(71) Applicant: Hitachi High-Technologies Corporation, Minato-ku, Tokyo (JP)

(72) Inventors: Masamichi Shiono, Tokyo (JP); Masako Nishimura, Tokyo (JP); Mami Konomi, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/376,425

(22) PCT Filed: Feb. 20, 2013

(86) PCT No.: PCT/JP2013/054067
§ 371 (c)(1),
(2) Date: Aug. 3, 2014

(87) PCT Pub. No.: WO2013/133012
PCT Pub. Date: Sep. 12, 2013

(65) Prior Publication Data
US 2014/0370540 A1  Dec. 18, 2014

(30) Foreign Application Priority Data

Mar. 9, 2012 (JP) ................................. 2012-052470

(51) Int. Cl.
| | |
|---|---|
| *G01N 1/30* | (2006.01) |
| *G01N 1/31* | (2006.01) |
| *C12M 1/00* | (2006.01) |
| *H01J 37/20* | (2006.01) |
| *G01N 1/34* | (2006.01) |
| *G01N 1/28* | (2006.01) |

(52) U.S. Cl.
CPC .. *G01N 1/30* (2013.01); *G01N 1/28* (2013.01);
*G01N 1/31* (2013.01); *G01N 1/34* (2013.01);
*H01J 37/20* (2013.01); *G01N 1/2806*
(2013.01); *H01J 2237/2608* (2013.01); *H01J 2237/28* (2013.01)

(58) Field of Classification Search
USPC ............ 250/306, 307, 309–311, 389, 390.04,
250/390.07, 461.2, 492.1, 492.21, 492.3,
250/526; 435/30, 40.5, 42, 284.1, 286.4,
435/286.5, 287.1, 288.7, 309.1, 325, 326,
435/347–354
See application file for complete search history.

(56) References Cited

U.S. PATENT DOCUMENTS 6,337,540 B1 * 1/2002 Corbin et al. ............. 315/111.21
7,354,733 B2 * 4/2008 Bukshpan et al. ............... 435/28
(Continued)

*Primary Examiner* — Bernard E Souw
(74) *Attorney, Agent, or Firm* — Miles & Stockbridge P.C.

(57) ABSTRACT

Disclosed is a method for enabling flexibility of the exoskeletons or joints of aquatic organisms immersed in an ion liquid water solution to be maintained without destroying their original forms by reducing the difference in osmotic pressure between the inside and outside of the aquatic organisms, preventing dehydration of biological samples. First, the aquatic organism is put into a low-concentration ionic liquid to increase continuously the concentration of the ionic liquid, enabling the water content of the aquatic organism to be substituted by a high-concentration ionic liquid in their original forms. The use of the increasing method that gentle increase in temperature of the ionic liquid by means of natural seasoning reduces the osmotic pressure difference between the inside and outside of the aquatic organism, increasing the concentration of the ionic liquid inside of the aquatic organism.

13 Claims, 6 Drawing Sheets

(56) References Cited

U.S. PATENT DOCUMENTS

| | | | |
|---|---|---|---|
| 8,343,769 B2* | 1/2013 | Kinoshita et al. | 436/18 |
| 2002/0198928 A1* | 12/2002 | Bukshpan et al. | 709/200 |
| 2009/0173882 A1* | 7/2009 | Kuwabata et al. | 250/307 |
| 2009/0280523 A1* | 11/2009 | Benabid et al. | 435/30 |
| 2012/0148553 A1* | 6/2012 | Hariri et al. | 424/93.71 |
| 2012/0270257 A1* | 10/2012 | Morris et al. | 435/29 |
| 2014/0264018 A1* | 9/2014 | Miwa et al. | 250/307 |

\* cited by examiner

METHODS FOR OBSERVING SAMPLES AND PREPROCESSING THEREOF

TECHNICAL FIELD

The present invention relates to a method for observing target objects, after water contained therein has been substituted by aqueous solution containing ionic liquid, under any of charged particle apparatuses such as an electron scanning microscope, and a method for pre-processing the target objects using a probe attached to the charged particle apparatus.

BACKGROUND ART

To conduct a research study on aquatic microorganisms, including minute crustaceans, such as copepod, cycrops, *daphnia, Gammarus*, euphasiid, *mysidopsis bahia*, cumacea, and triopsidae spp.; large crustaceans, such as nauplius, cypris, zoea, and mince larvae; zooplanktons, such as rotifer and ameba; and phytoplanktons, such as cyanophyceae, chlorophyta, and *symbiodinium* sp., morphological observation under a microscope is absolutely indispensable. In terms of taxonomy, in particular, for the larvae of minute crustaceans and large crustaceans, importance is given to morphological observation of fine legs called appendages. To make a detailed observation of the appendages of crustaceans, which are complicatedly entangled, the appendages need to be separated from each other for anatomy. Conventionally, the appendages of the crustaceans have been separated from each other for anatomy under a light microscope; however, control of anatomical devices is difficult under the light microscope, requiring skilled technique for anatomy.

In contrast, an electronic microscope with deep depth of focus is suitable to the observation of solid forms of living organisms and probes capable of controlling samples in the sample chamber of the electronic microscope are available. When aquatic microorganisms are taken out from water, however, for exposure to the atmosphere, they are too dried and shrunk to the degree that their original forms are not retained. The larvae of Minute crustaceans and large crustaceans, in particular, are deformed due to drying and shrinkage even when they are fixed using any of fixatives such as ethanol, glutaraldehyde, and formalin. When the aquatic organisms are observed under the electronic microscope, it is required to take out them from water or encapsulating medium and take them into a vacuum environment; for this reason, it has been difficult to observe the samples without pre-processing under the electronic microscope.

To solve this problem, methods for pre-processing samples for electronic microscope have been developed. A typical example of these methods is a method that prevents rupture of morphology of soft biological tissues using a low-vacuum cryostage for electron microscope capable of controlling the temperature of samples in the range from several tens of degrees below zero to room temperature in the low-vacuum atmosphere (1.3 to 270 Pa). For instance, in a nonpatent literature 1, it is disclosed that cryo-electron microscopy has been successfully achieved on *Ipomoea nil* leaf primordium using the aforementioned method.

On the other hand, a method using ionic liquid has been developed as a method for observing and controlling minute samples in a liquid under an electronic microscope. In Patent Literature 1, it is disclosed that such a property of ionic liquid that it does not evaporate even in vacuum is used to enable biological samples to be observed in their original forms under the electronic microscope. Disclosed are the methods, in particular, characterized in that samples containing water are immersed in the ionic liquid and then water is removed under vacuum; and the ionic liquid diluted with any of solvents such as alcohol is coated onto samples and then the solvent is removed under vacuum.

Since the aforementioned invention, the development of the methods for observing biological samples using ionic liquid has been promoted. For instance, in the nonpatent literature 2, it is reported that when ionic liquid was dripped on the colonies of acid-fast bacteria cultivated in an agar medium, which had been vapor-fixed with osmic acid, images, which seemed to be the original structures of the colonies of acid-fast bacteria, were obtained.

The patent literature 2 discloses that a certain ionic liquid enhances permeability into permeability into biological samples compared with other ionic liquid. In embodiments, the observation examples of the stems of *Undaria pinnatifida* and *Spinacia oleracea*, cotton tissue, hair, mouse bone, erythrocyte, and *Streptococcus mutans* are exemplified. Moreover, a method for impregnating, applying, and spraying a fluid medium, which is prepared by dissolving the ionic liquid in a polar solvent such as water, on the samples is disclosed.

CITATION LIST

Patent Literature

Patent Literature 1: International Publication No. WO2007/083756 (US2009/0173882)
Patent Literature 2: Japanese Unexamined Patent Application Publication No. 2011-137807

Nonpatent Literature

Nonpatent Literature 1: Kazuhiro UEDA, Mitsuhiko YAMADA, Machio GOTOH, Hisashi MATAUSHIMA, Kenzo KUBOKI, Attempt to observe samples at low temperatures under low-vacuum SEM, Proceedings of $49^{th}$ Academic Lectures, Japanese Society of Electron Microscope, P274, 1993
Nonpatent Literature 2: Mitsuru YOKOYAMA, Midori OGAWA, Takeshi ICHIHARA, Observation of acid-fast bacteria using ionic liquid under SEM, Proceedings of $27^{th}$ Academic Lecturers, Medical biological electronic microscope technology and general assembly program, P29, 2011

SUMMARY OF INVENTION

Technical Problem

In the patent literature 1, it is disclosed that such a property of the ionic liquid that it does not evaporate even in vacuum is used to enable biological samples to be observed in their original forms under the electronic microscope; however, there is such a problem that water contents of aquatic organisms is lost due to an osmotic pressure difference when the ionic liquid is directly coated on the aquatic organisms sensitive to a change in osmotic pressure or they are directly put in the ionic liquid, causing them to be dried up even in the ionic liquid.

Moreover, the method disclosed in the patent literature 1 may induce solvent bumping in vacuum because the ionic liquid diluted with solvent such as alcohol is coated on the samples and the solvent is removed under vacuum. In case of a bumping inside the shells of aquatic organisms (inside living organisms), the internal pressures of the shells suddenly increase, possibly causing the shell to be broken into small pieces and the small pieces to fly off. Thus, not only the samples may be broken but also the broken samples may contaminate a SEM sample chamber.

In the patent literature 2, the method for impregnating, applying, and spraying a fluid medium, which is prepared by dissolving the ionic liquid in a polar solvent such as water, on the samples is disclosed; however, no method for removing the solvent is disclosed at all.

An object of the present invention is to provide a method for observing samples under any of charged particle beam observation apparatuses such as an electronic microscope by suppressing a change in morphology and damage of the aquatic organisms sensitive to a change in osmotic pressure using the ion liquid water solution.

Solution to Problem

The method for observing the samples of the present invention is characterized in that it involves the steps of: immersing the target objects in a solution containing ionic liquid; drying the solution containing ionic liquid with the osmic pressures balanced between the solution containing ionic liquid and the inside of the target objects to increase the concentration of ionic liquid in the solution; and a charged particle beam is irradiated onto the target objects impregnated with ionic liquid therein to acquire the images of the target objects.

Advantageous Effects of Invention

According to the present invention, the aquatic organisms may be observed under any of charged particle beam observation apparatuses such as an electronic microscope by suppressing a change in morphology and damage of the aquatic organisms sensitive to a change in osmotic pressure using the ion liquid water solution.

DESCRIPTION OF EMBODIMENTS

Figure 1:
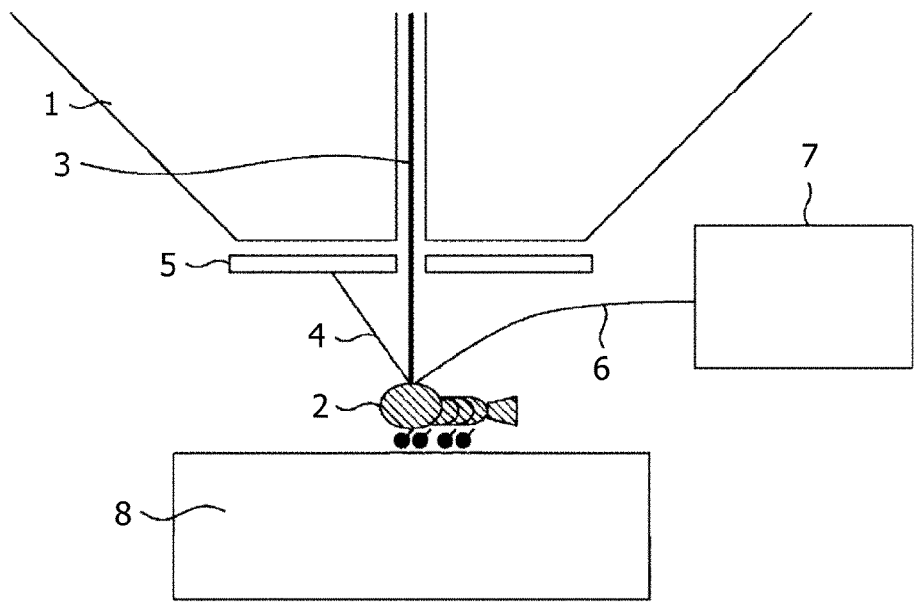
FIG. 1 is a side view of a sample chamber of an electronic microscope according to a first embodiment 1.

First, the problems with the conventional methods are explained in more detail.

The conventional method, which uses a vacuum air-drying step after a freezing step disclosed in Patent Literature 1, produces a problem that flexibility of joints and so like is lost, making it difficult to move legs and other movable parts of body. For this reason, when the aquatic organism is anatomized using a probe, etc. attached to the sample chamber of the electronic microscope, the dried aquatic organism may be damaged.

In the patent literature 1, it is disclosed that such a property of the ionic liquid that it does not evaporate even in vacuum is used to enable biological samples to be observed in their original forms under the electronic microscope; however, there is such a problem that water contents of aquatic organisms is lost due to an osmotic pressure difference when the ionic liquid is directly coated on the aquatic organisms sensitive to a change in osmotic pressure or they are directly put in the ionic liquid, causing them to be dried up even in the ionic liquid. Moreover, the method for applying the ionic liquid diluted with any of solvents such as alcohol, which may induce solvent bumping in vacuum because the solvent is removed under vacuum.

The method disclosed in the nonpatent literature 2 achieved a good result by dripping the ionic liquid on the colonies of acid-fast bacteria cultivated in an agar medium after vapor fixation with osmic acid. There is a problem, however, that dehydrating/broken effects due to an osmotic pressure difference between the ionic liquid and biological bodies may become considerably larger because the aquatic organisms such as minute crustaceans are far large in size compared with microorganisms such as acid-fast bacteria. Moreover, the vapor from osmic acid is high in toxicity, producing a safety problem. Even use of chemical fixation with glutaraldehyde alternative to vapor fixation with osmic acid does not make it to achieve easily as high mechanical strength as counteracting the breaking strength due to the osmotic pressure difference.

The patent literature 2 discloses the observation examples of the stems of *Undaria pinnatifida* and *Spinacia oleracea*, cotton tissue, hair, mouse bone, erythrocyte, and *Streptococcus mutans* are exemplified with no observation example of the aquatic organism. Since biological tissues described in the patent literature 2 are porous, the solvent is immediately permeated into the inside of the samples. In contrast, to conduct non-destructive observation of the forms of the aquatic organisms having a shell (exoskeleton) such as minute crustaceans, naturally, it is required to impregnate the ionic liquid throughout the individual organisms through their non-destructed exoskeleton, taking long time for immersion and drying compared with biological tissues. Moreover, since the exoskeletons of the aquatic organism may water shed, the aquatic organisms such as minute crustaceans need to be forcibly immersed in the ionic liquid in some cases. To solve this problem, any means fundamentally different from the method, which impregnates the ionic liquid into anatomized biological tissues or free cells, is need to be invented with respect to the method, which uses the ion liquid water solution for observing the aquatic organisms.

Moreover, in the patent literature 2, the method for impregnating, applying, and spraying a fluid medium, which is prepared by dissolving the ionic liquid in a polar solvent such as water, on the samples is disclosed; however, no method for removing the solvent is disclosed.

In the present invention, the aquatic organisms are first put into low-concentration ionic liquid (2 to 10%) to continuously increase the concentration of the ionic liquid, enabling the water content of the aquatic organisms to be substituted by the high-concentration of ionic liquid with the original forms of the living aquatic organisms retained. This may reduce the difference in osmotic pressure between the inside and outside of the aquatic organisms, preventing dehydration of the biological samples to enable flexibility of exoskeletons and joints of the aquatic organisms immersed in the ion liquid water solution to be retained without destructing the natural forms of the organisms. The use, in particular, of sluggish rise in temperature of the on liquid by natural seasoning reduces the osmotic pressure between the inside and outside of the aquatic organisms, achieving sluggish rise in concentrations of the ionic liquid in the aquatic organisms.

Hereinafter, by referencing to accompanying drawings, individual embodiments of the present invention are described.

It should be noted that the present invention is described taking a scanning electronic microscope (SEM) as an example, but not limited to SEM. The present invention may be applicable to sample observation by sample observation apparatuses using a scanning transmission electron microscope (STEM), ion microscope, and any of other types of charged particle beam.

In addition, the present invention is described taking the aquatic organisms as the examples of samples or target subjects, but not limited to them. The present invention is useful, in particular, for observing the observation objects sensitive to a change in osmotic pressure or drying. The observation objects may include aquatic microorganisms, for instance, minute crustaceans, such as copepod, cycrops, *daphnia*, *Gammarus*, euphasiid, *mysidopsis bahia*, cumacea, triopsidae spp.; large crustaceans, such as nauplius, cypris, zoea, mince larvae, and others; zooplanktons, such as rotifer and ameba; and phytoplanktons, such as cyanophyceae, chlorophyta, and *symbiodinium* sp.; observation objects sensitive to a change in osmotic pressure, such as water-absorbing resin, agar, gelatin, and *amorphophallus konjac*; observation objects, which may deform due to drying even under ordinary pressure, such as earthworm and pinworm; and observation objects, which are resistant to drying under ordinary pressure but deform under the vacuum condition, such as insects, tics, and spiders.

First Embodiment

FIG. 1 shows a side view of a sample chamber of an electronic microscope according to a first embodiment. The electronic microscope according to the first embodiment is a scanning electronic microscope, which is composed of an electron optical system including an electron gun for generating electron beams, a lens system for focusing the electron beams, and a deflector for deflecting the electron beams so as to scan on the samples; a control part for controlling the electron optic system; an image creation part for creating the images of the samples based on signals from a detector; any of indication parts, such as a display, for displaying the acquired images; an operation part, such as a mouse and console for operating the individual functions of the scanning electronic microscope; and a vacuum pump for vacuum-pumping columns having an electron source and electron optic system therein (not indicated in the figure). The sample chamber may be low-vacuum or high-vacuum pumped or another vacuum pump may be used to pump the sample chamber; in both cases, the samples are usually observed under the vacuum condition because the sample chamber of the electron microscope is kept in the vacuum state. It should be noted that the aforementioned control part and image creation part may be configured as hardware by means of special circuit boards or by means of a program, which is executed on a computer connected to the electronic microscope.

The inside of the sample chamber is composed of an objective lens 1 of the electronic microscope; an electron beam 3, which is irradiated from the objective lens 1 of the electronic microscope onto the sample 2 impregnated with the ion liquid water solution; a reflected electron detector 5, which detects a reflected electron signal 4 from the sample 2 impregnated with the ion liquid water solution; and a secondary electron detector 7, which detects a secondary electron signal 6 from the sample 2 impregnated with the ion liquid water solution. The secondary electrons, reflected electrons, and the like, which are obtained by irradiating electron beams onto the samples, are collectively referred to as secondary particles in some cases. The sample 2 impregnated with the ion liquid water solution is loaded on a sample stage 8 for the electronic microscope. The material for the sample stage is generally made of aluminum but the stage made of water-absorbing material, for instance carbon, may be used to use the effect of removal of excessive ionic liquid from the sample stage.

By reference to the first embodiment, taking *Gammarus*, which is one of main marine aquatic organisms, as samples, a method for observing the aquatic organism impregnated with the ion liquid water solution as the target samples is described. The aspect of the first embodiment is not limited to the *Gammarus* and may be applicable to observation of aquatic organisms typified by arthropods, planktons, and cultivated cells and observation of other samples sensitive to a change in osmotic pressure. The *Gammarus* used in the first embodiment are less than or equal to 3 mm in body length and have been immersed in ethanol solution with concentration of 90% or higher for one to four months; alternatively, the samples immediately after collection may be used.

Figure 2:
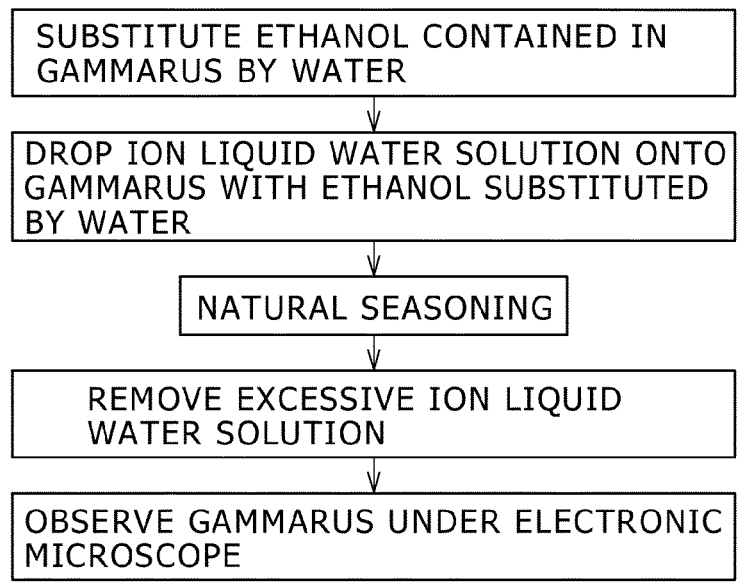
FIG. 2 is a view explaining a procedure for the method for observing samples according to the first embodiment.

FIG. 2 is a view explaining the procedure for acquiring the electronic microscopic image of the *Gammarus* according to the first embodiment of the present invention. First, the *Gammarus* stored in the ethanol solution are put into water to substitute the ethanol content thereof by water. At that time, the color of the *Gammarus*, which is translucent in the ethanol solution, changes into the opaque or white color after substitution by water. According to the first embodiment, the time, during which the *Gammarus* was immersed in water, is 80 min. but it may be shorter time provided that a change in body color is confirmed. Then, the *Gammarus* is pulled out from water, loaded on the sample stage for the electronic microscope, and an excessive water content is sucked with filter paper, etc. The aforementioned steps may be omitted when water is contained in the inside of the samples in advance as in the use of the *Gammarus* immediately after collection.

Figure 3:
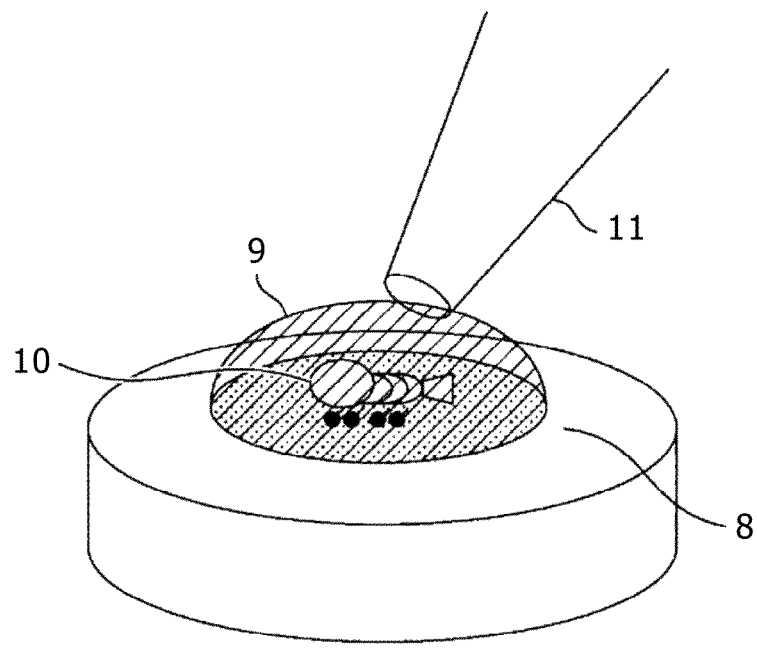
FIG. 3 is a view explaining the state where the ion liquid water solution is dripped on a *Gammarus* with ethanol substituted by water according to the first embodiment.

After sucking the excessive water content, a small amount of ionic liquid is dripped quickly on the samples with a pipette, etc. before they are dried up. FIG. 3 is a view explaining this state. In FIG. 3, the *Gammarus* 10, of which inside has been substituted by water is loaded on the sample stage 8. The ion liquid water solution 9 is dripped on the *Gammarus* with a pipette 11. Since the inside of the *Gammarus* 10 impregnated with water immediately after dripping, the body color of the *Gammarus* remains opaque or white.

For the *Gammarus*, the optimal concentration of the ion liquid water solution was 2% to 5%, but this concentration differs depending on the types of organisms or on the material, constitution, or osmotic pressure. From the standpoint of suppressing breakage or shrinkage of the sample due to a change in osmotic pressure, preferably, the concentration of ionic liquid in the aqueous solution is less than or equal to 10%. In the first embodiment, 20 ml of ion liquid water solution is used but it may be higher or lower concentration of ion liquid water solution may be used provided that the aquatic organism is immersed in the ion liquid water solution. The ionic liquid has preferably a hydrophilic property and in the first embodiment, the ionic liquid with the chemical formula $C_8H_{15}N_2BF_4$ was used. Moreover, an example of using water as a solvent for the ion liquid water solution is described but any other solvent may be used. Allowable solvents may include, for instance, ethanol, methanol, acetone, hexane, ether, and formalin including formaldehyde, in addition to water.

The *Gammarus* is dried in air for more than two hours after dripping the ion liquid water solution onto it. Drying in air means a method that leaves the sample as it is under the atmospheric pressure for a given time period to naturally evaporate the solvent (natural seasoning). Moreover, to accelerate a drying speed, a wind may be blown intentionally against the sample or the sample may be left as it is in a desiccator, in which temperature has been adjusted, or may be overheated. Thus, the terms of drying in air and natural seasoning used in the following paragraphs also include the state where the temperature or humidity is controlled. Control of the temperature or humidity enables the drying speed of the solvent to be controlled.

This means that such a method may be used that the solvent is removed so as to increase the concentration of the ionic liquid in the aqueous solution by drying the ion liquid water solution with the osmotic pressures balanced between the aqueous solution and the inside of the target object. According to the drying method in the first embodiment, the concentration of the ionic liquid in the aqueous solution increases continuously and gently. Moreover, according to the method described in the first embodiment, since the solvent is evaporated while the sample is immersed in ion liquid water solution, the balanced state may be kept between the osmotic pressures of the ion liquid water solution and of the inside of the target object.

A gentle increase in temperature from the temperature of a low-concentration (about 2 to 10%) initial solution of ionic liquid using natural seasoning may increase the concentration to the extent that sample is prevented from being broken due to the osmotic pressure difference and no breakage occurs due to drying even in vacuum.

Alternatively, it may be possible to prepare several ionic liquids with difference in concentration and increase sequentially the concentration of the solution, in which the sample is put; however, natural seasoning is far simple and convenient.

Figure 4:
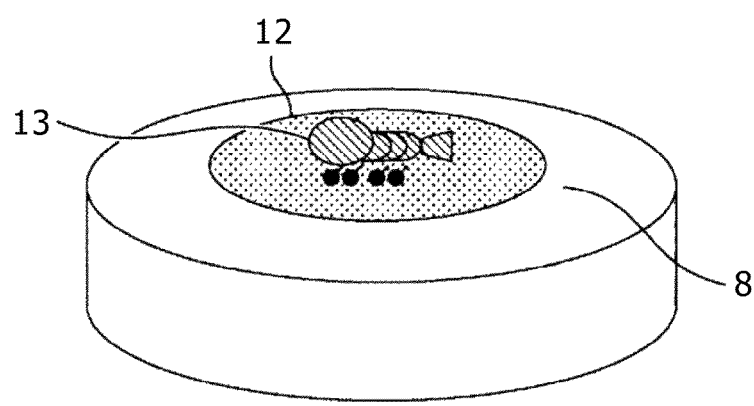
FIG. 4 is a view explaining the state where the *Gammarus* has been impregnated with the ionic liquid therein according to the first embodiment.

FIG. 4 is a view illustrating the state of the sample four hours after the state shown in FIG. 3. The ion liquid water solution decreases gradually in amount by means of drying in air, part of the *Gammarus* being possibly finally exposed. The concentration of the inside of the *Gammarus* 13 further increases so as to balance with the osmotic pressure of the ion liquid water solution 12 concentrated by means of drying in air. As the ion liquid water solution permeates deeply into the body of the *Gammarus*, the body color of the *Gammarus* changes from white into transparency. This enables it to be determined that the body of the *Gammarus* has been impregnated with the ionic liquid. Alternatively, the time for the standard sample body to be impregnated with the ionic liquid is measured in advance using the aforementioned method depending on a change in body color and it may be determined based on the immersion time whether the actual target sample has been impregnated with the ionic liquid. Also alternatively, it is not limited these methods whether the target object has been impregnated with the ionic liquid and may be determined based on, for instance, the weight of the target object.

During two to three hours of drying in air started after the ion liquid water solution is dripped on the sample, the amount of the ion liquid water solution continuously decreases; since then, no change is observed in amount of the ion liquid water solution, when drying in air is complete. The time for drying in air depends on the weather conditions and the dripping amount of the ion liquid water solution. At this point, since the osmotic pressures are equal to each other between the ion liquid water solution and the inside of the *Gammarus* no breakage occurs and the form of the sample may be retained even though it is left as it is for a period around clock or longer.

Figure 5:
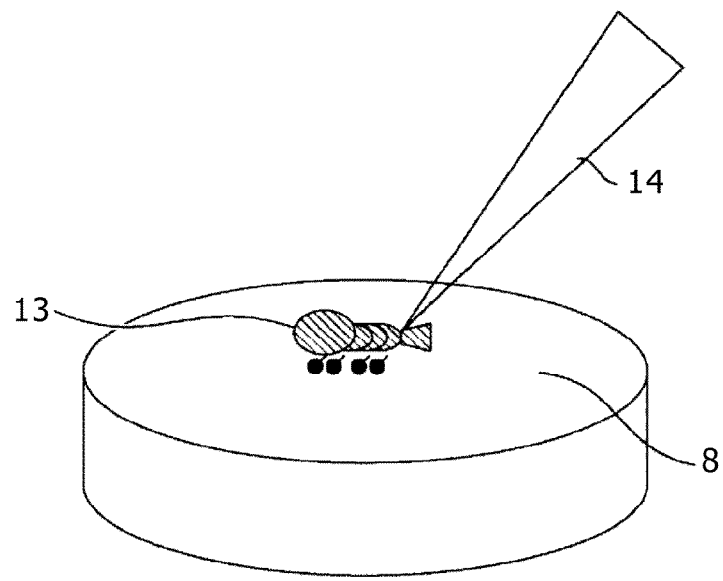
FIG. 5 is a view explaining a method for removing the ion liquid water solution attached to the minute sites such as the peripheries of legs by contacting the *Gammarus* with taper-shaped paper.

After drying in air, excessive ion liquid water solution is sucked with a wiping member 14 including a paper such as filter paper and gauze. As shown in FIG. 5, it is possible to remove the ion liquid water solution attached on the minute sites such as the peripheries of legs by contacting the *Gammarus* with the taper-shaped wiping member 14. At that time, it is possible to adsorb the ion liquid water solution attached to the minute sites, such as the apace between the legs by impregnating paper such as the filter paper and paper waste (Kimwipes (registered trademark), etc.) with water or a hydrophilic solution in advance. This is because the viscosity of the ion liquid water solution, which has increased on the sample surface due to drying, is decreased, enabling the ion liquid water solution to be easily absorbed by paper such as filter paper and paper waste, or gauze by contacting the sample surface with water or hydrophilic solution contained in them. In case of a difficulty in removing the ion liquid water solution, the sample may be washed with a low-concentration ion liquid water solution or water. Moreover, movement of the *Gammarus* onto a sample stage made of a water-absorbing material, for example, carbon further enhances the effect of removal of excessive ion liquid water solution.

Figure 6:
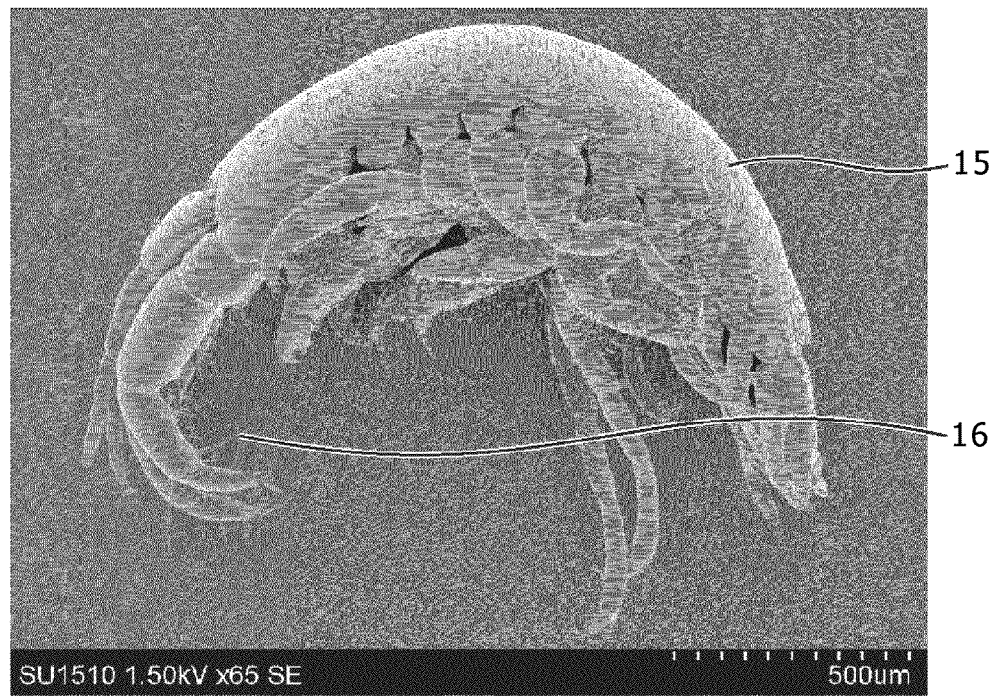
FIG. 6 is a view of an electronic microscopic image of the *Gammarus* according to the first embodiment.

After excessive ionic liquid is removed, the sample is observed under the electronic microscope. It is preferable that the electronic microscope used for observation is a scanning electronic microscope (SEM). FIG. 6 shows an image 15 of the *Gammarus* acquired by the electronic microscope using the method according to the first embodiment. This figure shows that the *Gammarus* may be acquired by the electronic microscope without changing or damaging the form sensitive to a change in osmotic pressure.

Figure 7:
FIG. 7 is an electronic microscopic image of the *Gammarus* seen from the back side according to the first embodiment.

Since the ion liquid water solution has been removed from the surface of the *Gammarus*, in FIG. 6, the minute structures, such as tactile seta 16, may be also observed without being covered with the ion liquid water solution. Since the *Gammarus*, of which water content has been substituted with the ion liquid water solution, retains its flexibility even after being put under vacuum, it is possible to observe the back side of the *Gammarus* reversed after the first observation under the electronic microscope, and to observe the *Gammarus* with the joints of legs moved after the first observation under the electronic microscope. FIG. 7 shows an image 17 of the back side of the *Gammarus*, which has been reversed and observed again under the electronic microscope after the first observation under the electronic microscope. This is the same specimen as that shown in FIG. 6 and FIG. 7 shows the opposite side of that observed in FIG. 6. The leg 18 shown in FIG. 7 has changed in its orientation because the joints of the leg were moved from the state shown in FIG. 6.

Figure 8:
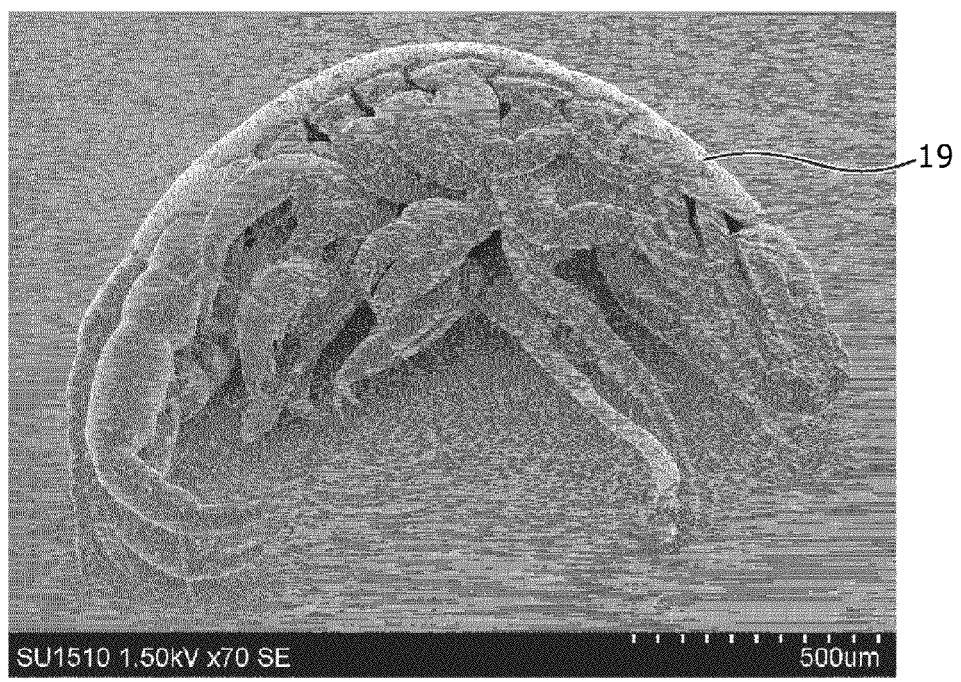
FIG. 8 is an electronic image of the *Gammarus* with a stage for the electronic microscope inclined at 45 degrees according to the first embodiment.

As shown in FIG. 7, the *Gammarus*, of which water has been substituted by the ion liquid water solution may be easily removed from the sample stage for the electronic microscope; moreover, it may be stably observed without slipping down even when the sample stage for the electronic microscope is inclined because it has been adsorbed on the sample stage by a trace amount of ion liquid water solution. FIG. 8 shows an electronic microscopic image 19 of the *Gammarus*, of which water has been substituted by the ion liquid water solution, and which is observed with the sample stage inclined at 45 degrees.

Figure 9:
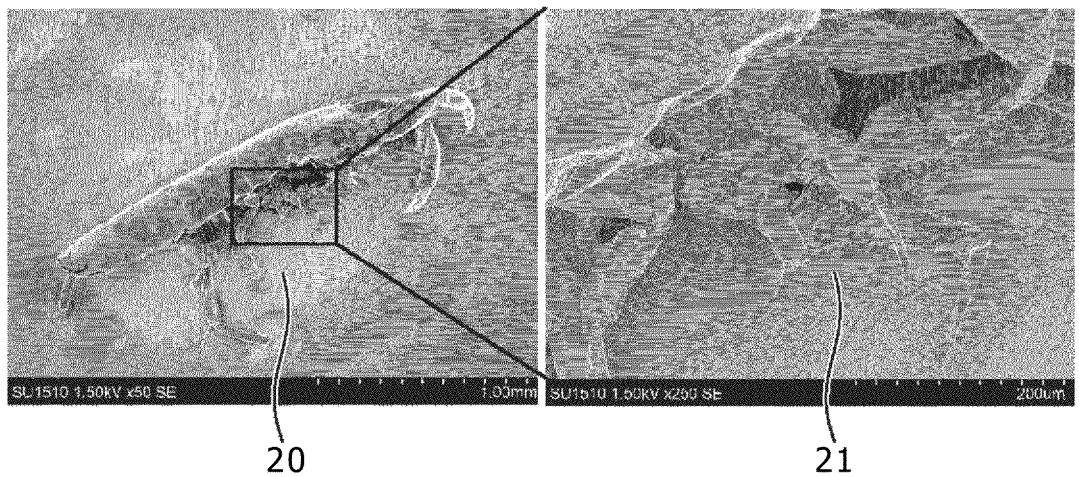
FIG. 9 is an electronic microscopic image of an observation example of the *Gammarus* without using the method according to the first embodiment.

For reference, FIG. 9 shows an example of observation of *Gammarus* without using the method according to the first embodiment. The left view shows an image 20 of the *Gammarus* observed without using the ionic liquid and the right view shows an electronic microscopic image 21 of the enlarged legs within a box at the center of the left figure. The example shown in FIG. 9 has been observed under the same conditions as those according to the first embodiment with the exception that the ionic liquid is used. It is obviously known that the moisture of the sample was lost and finally dried up when the *Gammarus* was observed at constant temperature without using the method according to the first embodiment. As known from the image labeled with the sign 21, in particular, the legs have been prominently deformed and broken.

The sample preparation method described above may be implemented using the sample preparation apparatus automatically or by following the user's instructions and operations. This type of sample preparation apparatus may be sometimes called a preprocessing apparatus. The sample preparation apparatus, which is used to implement the method according to the first embodiment, has at least an immersing part of immersing the target object in the aqueous solution containing the ionic liquid, and a drying part of increasing the concentration of the ionic liquid in the aqueous solution containing the ionic liquid by drying the aqueous solution containing the ionic liquid with the osmotic pressures balanced between the aqueous solution containing the ionic liquid and the inside of the target object. Herein, the immersing part may be, for instance, a device for collecting a small amount of aqueous solution containing the ionic liquid and dripping it onto the target object, such as a micropipette. The drying part may be a sample chamber, in which the target object is put under the atmospheric pressure, or may be a desiccator, etc. capable of controlling the temperature and humidity. Alternatively, the drying time period may be controlled by a timer installed at the sample preparation apparatus provided that the time required for drying has been determined in advance.

Moreover, since the sample preparation apparatus has a light microscope capable of observing the target object being dried in the drying part, it is possible to check the degree of reduction in ionic liquid due to drying and determine whether the target object has not been shrunk or deformed by the ionic liquid. In addition, as mentioned above, the sample preparation apparatus is useful for determining whether the target object has been impregnated with e ionic liquid based on a change in color of the target object.

Furthermore, according to the first embodiment, the aqueous solution containing the ionic liquid remaining after drying is sucked with the wiping member 14, for instance paper such as filter paper and gauze; it is possible to attach the same type of wiping member to the sample preparation apparatus to remove the aqueous solution containing the ionic liquid remaining after drying in the drying part.

Additionally, by attaching, a part for sensing the progress of drying of the aqueous solution containing the ionic liquid based on a change in weight of the target object, to the sample preparation apparatus, it is possible to determine conveniently whether the target object has been impregnated with the ionic liquid.

Second Embodiment

By reference to a second embodiment, described are the methods for observing an aquatic organism impregnated with ion liquid water solution taking a copepod (cycrops), which is one of marine aquatic organisms, as a sample; and for preparing prepared slides for a light microscope using the aquatic organism impregnated with the ion liquid water solution. The descriptions of the same parts as those in the first embodiment are omitted in the following paragraphs. The copepods used in the second embodiment is less than or equal to 2 mm in body length and has been stored in ethanol solution with concentration of 90% or more for one month; however, the samples immediately after collection may be used.

First, the copepod stored in the ethanol solution is put into water to substitute ethanol by water. At that time, the body color, which is translucence in the ethanol solution, changes into opaque or white after substitution by water. According to the second embodiment, the time required for copepod to be immersed is 80 min. but it may be shorter provided that a change in body color can be checked. Next, the copepod is pulled up from water, loaded on the sample stage for electronic microscope, and excessive water is sucked with filter paper, etc. The above-mentioned steps may be omitted when water has been contained in the sample, for instance a *Gammarus* immediately after collection is used.

Before the sample is dried up after excessive water is sucked, a small amount of ionic liquid is quickly dripped with a pipette, etc. by the method shown in FIG. 3. For the copepod, the optimal concentration of the ion liquid water solution 10% but depends on the types of organisms, or on the materials, compositions, and osmotic pressures. According to the second embodiment, 20 ml ion liquid water solution is used; however, it is possible to use a larger or smaller amount of ion liquid water solution provided that the aquatic organism can be immersed in water. The ionic liquid has preferably a hydrophilic property and in the second embodiment, the ionic liquid represented by the chemical formula $C_8H_{15}N_2BF_4$. The example, in which water is used as a solvent for the ion liquid water solution, is taken; however, it is possible to use any other solvent. In addition to water, the solvents may include, for instance ethanol, methanol, acetone, hexane, ether, and formalin including formaldehyde.

For more than two hours after the ion liquid water solution is dripped onto the copepod, drying in air is performed. The term drying in air has the same meaning as that in the first embodiment; namely, the ion liquid water solution is dried with the osmotic pressures balanced between the ion liquid water solution and the inside of the target object, meaning commonly the methods for removing solvents by means of continuously increasing the concentration of the ionic liquid in the aqueous solution. The amount of ion liquid water solution is gradually decreased by drying in air and finally part of copepod may be sometimes exposed. As the ion liquid water solution permeates into the copepod body, the body color of the copepod changes from white to transparent. Based on this change, it may be determined that the body of the *Gammarus* has been impregnated with the ionic liquid. Alternatively, it is possible that the time required for the ionic liquid to permeate into the inside of the standard sample is measured in advance and it is determined based on the immersion time whether the target sample has been impregnated with the ionic liquid. During about two to three hours after the start of drying in air after the ion liquid water solution is dripped, the amount of ion liquid water solution is continuously decreased, and then no change in amount of ion liquid water solution is observed and drying in air is complete. The time for drying in air depends on the weather conditions and the amount of dripped ion liquid water solution. At that time, since the osmotic pressures are balanced between the ion liquid water solution and the inside of the copepod, the sample is not broken and its form is retained even through it is left as it is round the clock or more.

After drying in air is complete, excessive ion liquid water solution is sucked with any of the wiping members such as paper including filter paper and paper waste, and gauze. The method for sucking excessive ion liquid water solution is as shown in FIG. 5. At that time, by impregnating paper such as the filter paper or KimWipe, or gauze with water or hydrophilic solution in advance, the ion liquid water solution attached to the minute sites, for instance the space between the legs, may be adsorbed. This is because the viscosity of the ion liquid water solution, which has increased on the sample surface due to drying, is decreased, enabling the ion liquid water solution to be easily absorbed by paper such as filter paper and paper waste, or gauze by contacting the sample surface with water or hydrophilic solution contained in them. In case of a difficulty in removing the ion liquid water solution, the sample may be washed with a low-concentration ion liquid water solution or water. Moreover, movement of the *Gammarus* onto a sample stage made of a water-absorbing material, for instance carbon, further enhances the effect of removal of excessive ion liquid water solution.

Figure 10:
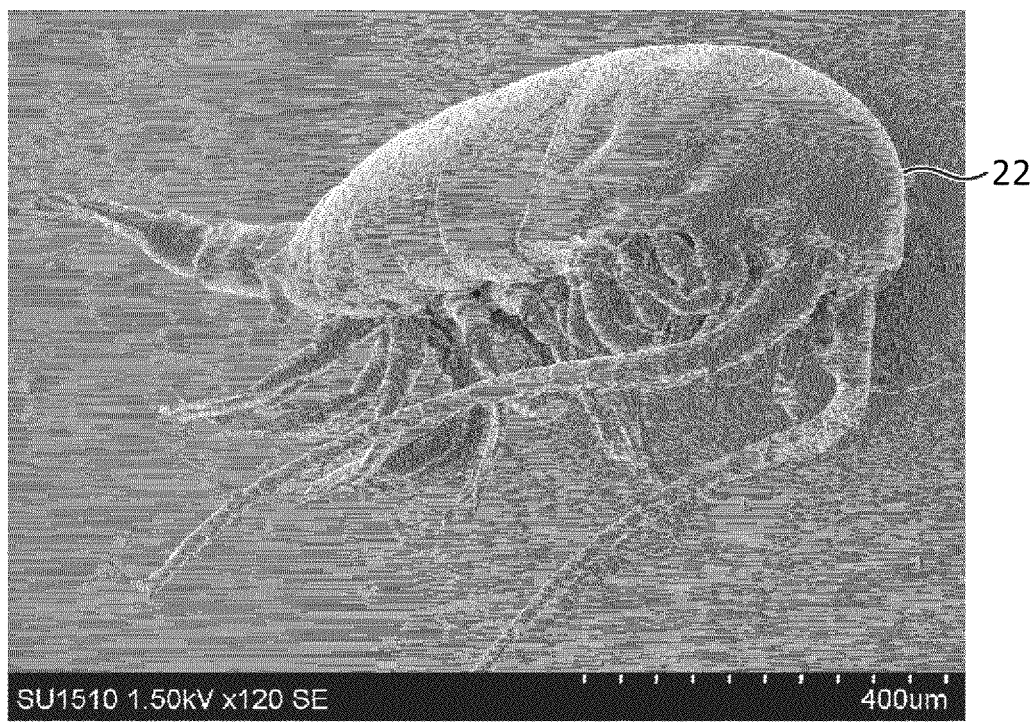
FIG. 10 is an electronic microscopic image of a copepod according to a second embodiment.

After excessive ionic liquid is removed, the sample is observed under the electronic microscope. It is preferable that the electronic microscope used for observation is a scanning electronic microscope (SEM). The fundamental configuration of the SEM is as described in the first embodiment. FIG. 10 shows an image 15 of the *Gammarus* acquired by the electronic microscope using the method according to the second embodiment. This figure shows that the *Gammarus* may be acquired by the electronic microscope without changing or damaging the form sensitive to a change in osmotic pressure. The electronic microscopic image 22 shown in FIG. 10 was acquired with the sample stage inclined at 45 degrees, making it clear that the sample may be observed at the inclined position.

Figure 11:
FIG. 11 is an electronic microscopic image of an observation example of the copepod without using the method according to the second embodiment.

For reference, in FIG. 11, an example of observation of a copepod without using the method according to the second embodiment is shown. In the example shown in FIG. 11, the sample is observed under the same conditions as those of second embodiment with the exception that the ionic liquid is used. As known from the electronic microscopic image 23 shown in FIG. 11, the copepod is very sensitive to dryness and was prominently deformed at constant temperature and constant pressure. It is impossible to observe the copepod dried at constant temperature without using the method according to the second embodiment.

Generally, the copepod is observed under a light microscope. The method for preparing the target samples according to the second embodiment eliminates the need for fixing the sample on the sample stage with any of adhesive materials such as a carbon tape or carbon paste because the sample is adsorbed on the sample stage by means of a trace amount of ion liquid water solution. Accordingly, it is possible that the aquatic organism is removed from the special sample stage for the electronic microscope after observation and anatomy under the electronic microscope and the aquatic organism as a sample is encapsulated with water or any other encapsulating medium to prepare the prepared slides for the light microscope. It is possible that the copepod, in which water has been substituted with the ion liquid water solution after the observation under the electric microscope, is observed under the electronic microscope by encapsulating with water or any of encapsulating media such as Canada balsam.

The copepod, which has been processed by the conventional freeze-drying method, has cavities formed therein and it is difficult to penetrate water or Canada balsam into the cavities, producing a problem that air bubbles generate. In contrast, the method according to the second embodiment does not form cavities in the copepod with the inside of the copepod impregnated with the ion liquid water solution; accordingly, the prepared slides for the light microscope may be prepared with no concern about air bubbles being generated in the inside of the aquatic organism.

The method according to the second embodiment may be performed using the sample preparation apparatus according to the first embodiment. Moreover, such a part of preparing samples for the light microscope may be attached to the sample preparation apparatus that an encapsulating medium is dripped onto the target object to prepare the prepared slides for the electronic microscope.

Third Embodiment

In terms of taxonomy for the larvae of minute crustaceans and large crustaceans, importance is given to morphological observation of fine legs called appendages. To make a detailed observation of the appendages of crustaceans, which are complicatedly entangled, the appendages need to be separated from each other for anatomy. Conventionally, the appendages of the crustaceans have been separated from each other for anatomy under a light microscope; however, control of anatomical devices is difficult under the light microscope, requiring skilled technique for anatomy. This embodiment explains a method for anatomizing the crustaceans under the electronic microscope to solve this problem. The descriptions of the same parts as those in the first embodiment are omitted in the following paragraphs.

Figure 12:
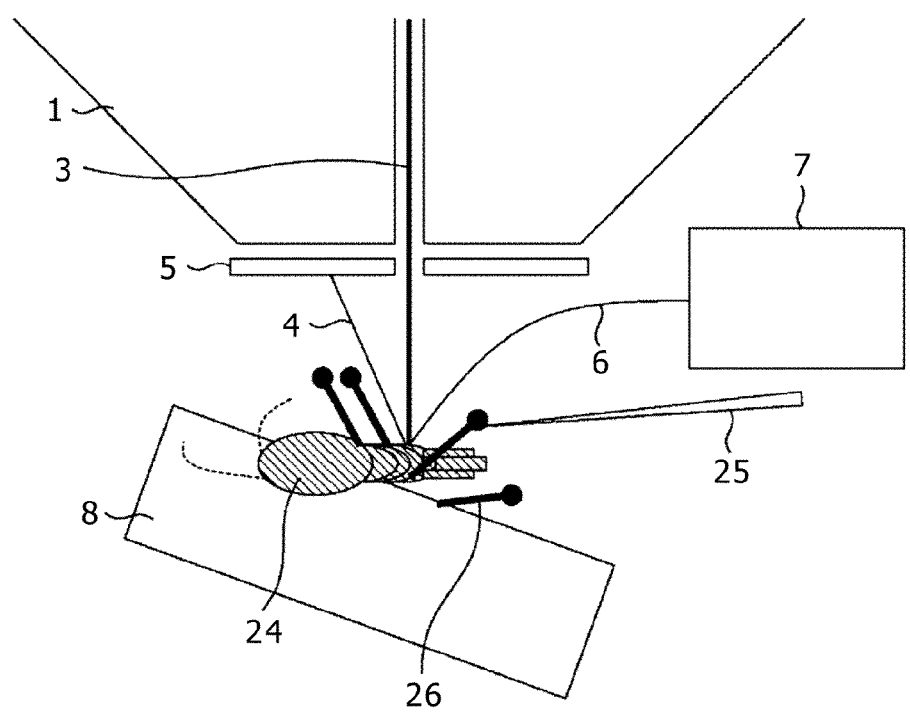
FIG. 12 is a view explaining a procedure for anatomizing aquatic organisms impregnated with the ion liquid water solution under the electronic microscope using a probe attached to the sample chamber.

FIG. 12 is a view explaining that the aquatic organism, which has acquired flexibility through impregnation with the ion liquid water solution, is anatomized under the electronic microscope using a probe attached in the sample chamber of the electric microscope. The aquatic organism 24 shown in FIG. 12, which has acquired flexibility through impregnation with the ion liquid water solution, is the sample undergoing the process according to the first or second embodiment. The probe 25 attached to the inside of the sample chamber of the electronic microscope is preferably capable of controlling while observing the sample under the electronic microscope. Handling the sample during acquisition of an image by means of electron beams enables moving images of the sample to be acquired, the moving state of the sample being visually recognized.

When the orientation of the aquatic organism 24 is not suitable for anatomy, the aquatic organism 24 is rotated by rolling over using the probe 25. The state of the rolled aquatic organism is as shown in FIG. 7. As known from FIG. 12, an explaining view, the sample stage for the electronic microscope is capable of being inclined if necessary.

After the orientation of the aquatic organism 24 is adjusted, the joints of the appendages are moved or the appendages are separated for anatomy using the probe 25. At that time, if two or more probes have been attached to the sample chamber of the electronic microscope, this operation is made easier. Accordingly, two or more proves have been preferably attached to the sample chamber of the electronic microscope. The legs 26 of the aquatic organism anatomized using the probe 25 attached to the sample chamber of the electronic microscope have been separated using the probe 25.

The method according to the third embodiment, that observes the aquatic organism, in which water or any other solution has been substituted by the ion liquid water solution, has the effect that since the joints do not lose flexibility even in the high vacuum environment in the electronic microscope, the moving parts such as legs may be moved. Accordingly, the method has a further effect that after or during the observation under the electronic microscope, the aquatic organism may be observed while the moving parts such as legs of the aquatic organism being moved using the probe attached to the sample chamber of the electronic microscope. Furthermore, the aquatic organism as a sample may be anatomized.

The anatomized legs of the aquatic organism, in which water has been substituted by the ion liquid water solution, have a conductive property. Accordingly, it is possible to reduce flying of broken pieces of the sample associated with charge-up phenomenon and contamination of the sample chamber of the electronic microscope due to flying of broken pieces. Moreover, the aquatic organism, in which water has been substituted with the ion liquid water solution, retains flexibility, allowing to be handled such as bending of the appendages with no damage to the sample.

The anatomized sample may be observed as it is under the electronic microscope; however, it may be re-observation using any of other analyzers such as a light microscope if necessary. In this case, following the method according to the second embodiment, the prepared slides may be prepared using an encapsulating medium. When the biological microscope is used for observation, the aforementioned steps may be performed on the slide glass for the light microscope or on the cover glass. Generally, glass is an insulating material, causing charge-up phenomenon; applying a thin film of ionic liquid on the glass surface may add the conductive property.

The present invention is not limited to the aforementioned embodiments and may include a various types of variations. For instance, the aforementioned embodiments are described in detail for easy understanding of the present invention and always not to limited to the method including all the described steps. Moreover, part of the method according to an embodiment may be substituted by that of the method according to other embodiment and part of the method according to an embodiment may be added to that of the method according to other embodiment. Furthermore, parts of the methods according to the individual embodiments may be added to, deleted from, substituted with those of the methods according to other embodiments.

LIST OF REFERENCE SIGNS

1 Objective lens
2 Sample
3 Electron beam
4 Reflected electron signal
5 Reflected electron detector
6 Secondary electron signal
7 Secondary electron detector
8 Sample stage
9 Ion liquid water solution
10 *Gammarus* with ethanol substituted by water
11 Pipette
12 Concentrated ion liquid water solution
13 *Gammarus*
14 Swabbing member
15 Electronic microscopic image of *Gammarus* with water substituted by the ion liquid water solution
16 Tactile seta of the *Gammarus*
17 Electric microscopic image of the back side of the *Gammarus*, which was reversed and observed under the electronic microscope again after the first observation under the electronic microscope.
18 Leg of which joints have been moved after the first observation under the electronic microscope
19 Electric microscopic image of the *Gammarus* with water substituted by the ion liquid water solution, which was observed by inclining the sample stage of the electronic microscope at 45 degrees
20 Electronic microscopic image of the *Gammarus* observed without using the ionic liquid
21 Enlarged electronic microscopic image of the legs of the *Gammarus* deformed by means of drying
22 Electronic microscopic image of a copepod with water substituted by the ion liquid water solution
23 Electronic microscopic image of the copepod observed without using the ionic liquid
24 Aquatic organism
25 Probe
26 Legs of the aquatic organism The invetion claimed is:

1. A method for observing samples that acquires the images of a target object by detecting a signal obtained by means of irradiating charged particle beams onto the target object comprising the steps of:
   immersing the target object into an aqueous solution containing an ionic liquid;
   drying for increasing the concentration of the ionic liquid in the aqueous solution containing the ionic liquid by drying the aqueous solution containing the ionic liquid with the osmotic pressures balanced between the aqueous solution containing the ionic liquid and the inside of the target object; and
   observing for acquiring the image of the target object by means of irradiating the charged particle beams on the target object impregnated with the aqueous solution containing the ionic liquid.

2. The method for observing the samples according to claim 1, further comprising the step of impregnating the target object, wherein the end of the drying step is determined based on a change in color of the target object.

3. The method for observing the samples according to claim 1, wherein the ionic liquid has a hydrophilic property.

4. The method for observing the samples according to claim 3, further comprising the step of removing the aqueous solution containing the ionic liquid using a member impregnated with water or hydrophilic solution after the drying step.

5. The method for observing the samples according to claim 1, wherein the concentration of the ionic liquid in the aqueous solution containing the ionic liquid used in the immersing step less than or equal to 10%.

6. The method for observing the samples according to claim 1, further comprising the steps of preparing a prepared slides for a light microscope by encapsulating the target object impregnated with the aqueous solution containing the ionic liquid with an encapsulating medium; and observing the prepared sides for the light microscope under the light microscope.

7. The method for observing the samples according to claim 1, further comprising the step of breaking down or anatomizing the target object impregnated with the aqueous solution containing the ionic liquid using a probe.

8. A method for pre-processing samples to be observed using an apparatus for acquiring the images of the samples by detecting a signal obtained by means of irradiating electro particle beams onto the samples, comprising the steps:
   immersing the samples into the aqueous solution containing the ionic liquid; and
   drying for increasing the concentration of the ionic liquid by drying the aqueous solution containing the ionic liquid with the osmotic pressures balanced between the aqueous solution containing the ionic liquid and the inside of the samples.

9. A sample preparation apparatus for preparing a target object into the state suitable for observation using a sample observation apparatus, which obtains the image of the target object by detecting a signal obtained by means of irradiating charged particle beams onto the target object comprising:
   an immersing part of immersing the target object into an aqueous solution containing ionic liquid; and
   a drying part of increasing the concentration of the ionic liquid in the aqueous solution containing the ionic liquid by drying the aqueous solution containing the ionic liquid with the osmotic pressures balanced between the aqueous solution and the inside of the target object.

10. The sample preparation apparatus according to claim 9, further comprising a light microscope capable of observing the target object being dried in the drying step.

11. The sample preparation apparatus according to claim 9, further comprising a part of removing the aqueous solution containing the ionic liquid remaining after the drying step in the drying part.

12. The sample preparation apparatus according to claim 9, further comprising a part of detecting the progress of drying of the aqueous solution containing the ionic liquid based on a change in weight of the target object.

13. The sample preparation apparatus according to claim 9, wherein the immersing part is a micropipette for dripping the aqueous solution containing the ionic liquid onto the target object.

* * * * *